(12) United States Patent
Calos

(10) Patent No.: US 7,842,503 B2
(45) Date of Patent: Nov. 30, 2010

(54) HYBRID RECOMBINASES FOR GENOME MANIPULATION

(75) Inventor: Michele P. Calos, Burlingame, CA (US)

(73) Assignee: Poetic Genetics, LLC, Burlingame, CA (US)

( * ) Notice: Subject to any disclaimer, the term of this patent is extended or adjusted under 35 U.S.C. 154(b) by 623 days.

(21) Appl. No.: 11/547,371

(22) PCT Filed: Apr. 29, 2005

(86) PCT No.: PCT/US2005/015101

§ 371 (c)(1), (2), (4) Date: Oct. 29, 2007

(87) PCT Pub. No.: WO2005/107790

PCT Pub. Date: Nov. 17, 2005

(65) Prior Publication Data

US 2008/0241116 A1    Oct. 2, 2008

Related U.S. Application Data

(60) Provisional application No. 60/566,904, filed on Apr. 30, 2004.

(51) Int. Cl.
*C12N 15/00* (2006.01)
*C12N 15/87* (2006.01)
*C12N 9/00* (2006.01)
*C12P 21/06* (2006.01)
*C12P 19/34* (2006.01)
*C07H 21/04* (2006.01)
*A61K 38/43* (2006.01)

(52) U.S. Cl. .................. 435/440; 435/455; 435/462; 435/69.1; 435/320.1; 435/91.1; 435/183; 536/23.2; 424/94.1

(58) Field of Classification Search .................. 435/440, 435/455, 462, 320.1, 183, 69.1; 536/23.2; 424/94.1
See application file for complete search history.

(56) References Cited

U.S. PATENT DOCUMENTS

2002/0094516 A1 *   7/2002   Calos et al. .................... 435/4

FOREIGN PATENT DOCUMENTS

WO    2004009792    1/2004

WO    WO 2004/029233 A2    4/2004

OTHER PUBLICATIONS

Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Nunes-Duby e al., Similarities and differences among 105 members of the Int family of site-specific recombinases. Nuc Acids Res., 1998, vol. 26(2): 391-406.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650. Enablement.*
Gregory et al., Integration site for *Streptomyces* phage phiBT1 and development of site-specific integrating vectors. J. Bacteriol., 2003, vol. 185 (17): 5320-5323.*
Kuhstoss et al., Analysis of the integration function of the Sreptomycete bacteriophage phiC31. J. Mol. Biol., 1991, vol. 222: 897-908.*
Akopian A et al., Chimeric recombinases with designed DNA sequence recognition: Proceedings of the National Academy of Sciences of USA, National Academy of Science, Washington D.C.; vol. 100 No. 15; Jul. 2003 pp. 8688-8691.
Gregory M. et al., "Integration site for *Streptomyces* phage ph1BTI and development of site-specific integrating vectors" Journal of Bacteriology; Sep. 2003 vol. 185, No. 17; pp. 5320-5323.
Groth, A.C., et al., "Phage Integrases: Biology and Applications"; Journal of Molecular Biology, London, GB; vol. 335, No. 3, Jan. 2004 pp. 667-678.
Shaikh A.C., et al. "Chimeras of the Flp and Cre recombinases: tests of the 18-23 mode of cleavage by flp and cre"; Journal of Molecular Biology, London, GB; vol. 302, No. 1; Sep. 2000 pp. 27-48.
Smith, M et al., Diversity in the Serine Recombinases:; Molecular Microbiology, Wiley-Blackwell Publishing Ltd, GB; vol. 44, No. 2; Jan. 2002 pp. 299-307.
Yagil, E. et al., "Identifying determinants of recombination specificity: Construction and characterization of chimeric bacteriophage integrases"; Journal of Molecular Biology; vol. 252, No. 2 (1995) pp. 163-177.

* cited by examiner

*Primary Examiner*—Ganapathirama Raghu
(74) *Attorney, Agent, or Firm*—Edward J. Baba; Lynn J. Kidder; Bozicevic, Field & Francis LLP

(57) ABSTRACT

The present invention provides methods to site-specifically manipulate genomes by using hybrid recombinases. Hybrid recombinases comprise a modified catalytic domain from a unidirectional serine phage integrase, fused to a foreign DNA recognition domain.

12 Claims, 6 Drawing Sheets

HYBRID RECOMBINASES FOR GENOME MANIPULATION

BACKGROUND OF THE INVENTION

The current inability to perform efficient, site-specific integration of incoming DNA into the chromosomes of higher organisms is holding up advances in basic and applied biology. Recently strategies for chromosomal integration that take advantage of the high efficiency and tight sequence specificity of recombinase enzymes isolated from microorganisms have been described. In particular, a class of phage integrases that includes the phiC31 integrase (Kuhstoss, S., and Rao, R. N., J. Mol. Biol. 222, 897-908 (1991); Rausch H., and Lehmann, M., Nucleic Acids Research 19, 5187-5189 (1991)) have been shown to function in mammalian cells (Groth, A. C., et al., Proc. Natl. Acad. Sci. USA 97, 5995-6000 (2000)).

Such site-specific recombinase enzymes have long DNA recognition sites that are typically not present even in the large genomes of mammalian cells. However, it has been recently demonstrated that recombinase pseudo sites, i.e. sites with a significant degree of identity to the wild-type binding site for the recombinase, are present in these genomes (Thyagarajan, B., et al., Gene 244, 47-54 (2000)).

The present disclosure teaches compositions and methods to generate hybrid integrases that involve fusing an improved catalytic domain having integrase activity with a foreign DNA binding domain, providing site-specificity for the integration reaction.

SUMMARY OF THE INVENTION

Such hybrid recombinases can mediate efficient site-specific recombination in vitro and in a wide range of cells and species and are useful for creating insertions, deletions, and other genome modifications. These modifications are valuable, for example, for gene therapy, construction and manipulation of cell lines and transgenic organisms, and protein production.

SUMMARY OF THE DRAWINGS

FIG. 2A. Plasmid pWT-C was used to generate phiBT1-phiC31 hybrid integrases. It contains the C-terminal portion of the phiC31 integrase with a CMV promoter in front. N-terminal regions from phiBT1 integrase were cloned into the EcoRI and PstI sites in frame with the C-terminal phiC31 integrase to generate hybrids 120 and 168. FIG. 2B. pBP-Green was used to determine extra-chromosomal recombination efficiency in 293 cells. This "flipper" plasmid contains the CMV promoter flanked by inverted phiC31 att sites. Recombination between the att sites inverts the CMV promoter to the active orientation, resulting in expression of the GFP gene.

DETAILED DESCRIPTION OF THE INVENTION

Figure 1:
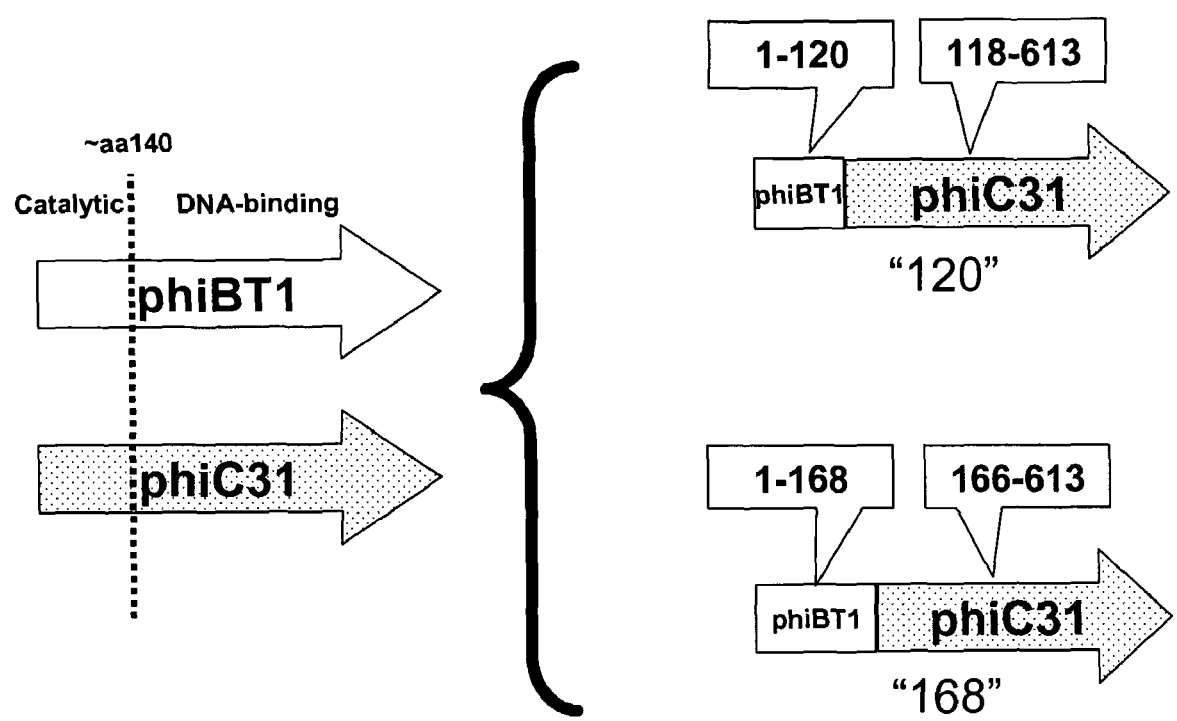
FIG. 1 is a schematic diagram of phiBT1-phiC31 hybrids 120 and 168. Hybrid 120 carries amino acids 1-120 from phiBT1 integrase and amino acids 118-613 from phiC31 integrase. Hybrid 168 has amino acids 1-168 from phiBT1 integrase and amino acids 166-613 from phiC31 integrase.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

1. Definitions

The term "recombinases," as used herein, refers to a family of enzymes that mediate site-specific recombination between specific DNA sequences recognized by the recombinase (Esposito, D., and Scocca, J. J., Nucleic Acids Research 25, 3605-3614 (1997); Nunes-Duby, S. E., et al., Nucleic Acids Research 26, 391-406 (1998); Stark, W. M., et. al., Trends in Genetics 8, 432-439 (1992)).

The term "altered recombinases" as used herein, refers to recombinase enzymes in which the native, wild-type recombinase gene found in the organism of origin has been mutated in one or more positions. An altered recombinase possesses a DNA binding specificity and/or level of activity that differs from that of the wild-type type enzyme. Altered recombinases are disclosed in more detail in U.S. Pat. No. 6,808,925, which is incorporated herein by reference in its entirety for all purposes.

The term "hybrid recombinase" as used herein refers to a recombinase containing an enhanced catalytic domain and a DNA binding domain that can be non-native.

The term "wild-type recombination site (RS/WT)", as used herein, refers to a recombination site normally used by an integrase or recombinase. For example, lambda—is a temperate bacteriophage that infects E. coli. The phage has one attachment site for recombination (attP) and the E. coli bacterial genome has an attachment site for recombination (attB). Both of these sites are wild-type recombination sites for lambda-integrase. In the context of the present invention, wild-type recombination sites occur in the homologous phage/bacteria system. Accordingly, wild-type recombination sites can be derived from the homologous system and associated with heterologous sequences, for example, the $Att_B$ site can be placed in other systems to act as a substrate for the integrase.

The term "pseudo recombination site (RS/P)" as used herein refers to a site at which recombinase can facilitate recombination even though the site may not have a sequence identical to the sequence of its wild-type recombination site. A pseudo-recombination site is typically found in an organism heterologous to the native phage/bacterial system. For example, a phiC31 integrase and vector carrying a phiC31 wild-type recombination site can be placed into a eukaryotic cell. The wild-type recombination sequence aligns itself with a sequence in the eukaryotic cell genome and the integrase facilitates a recombination event. When the sequence from the genomic site, in the eukaryotic cell, where the integration of the vector took place (via a recombination event between the wild-type recombination site in the vector and the genome) is examined, the sequence at the genomic site typically has some identity to but may not be identical with a wild-type phiC31 recombination site. The recombination site in the eukaryotic cell is considered to be a pseudo recombination site at least because the eukaryotic cell is heterologous to the normal phage/bacterial cell system. The size of the pseudo-recombination site can be determined through the use of a variety of methods including, but not limited to, (i) sequence alignment comparisons, (ii) secondary structural comparisons, (iii) deletion or point mutation analysis to find the functional limits of the pseudo-recombination site, and (iv) combinations of the foregoing. Pseudo recombination sites typically occur naturally in the genomes of eukaryotic cells (i.e., the sites are native to the genome) and are functionally identified as described herein.

The term "pseudo attP site" or "pseudo attB site," as used herein refers to pseudo sites that are similar to wild-type phage or bacterial attachment site sequences, respectively, for phage integrase enzymes. "Pseudo att site" is a more general term that can refer to either a pseudo attP site or a pseudo attB site.

A recombination site "native" to the genome, as used herein, means a recombination site that occurs naturally in the genome of a cell (i.e., the sites are not introduced into the genome, for example, by recombinant means.)

By "nucleic acid construct" it is meant a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

By "nucleic acid fragment of interest" it is meant any nucleic acid fragment that one wishes to insert into a genome. Suitable examples of nucleic acid fragments of interest include therapeutic genes, marker genes, control regions, trait-producing fragments, and the like.

"Therapeutic nucleic acids" or "therapeutic genes" are those nucleic acid sequences which encode molecules that provide some therapeutic benefit to the host, including proteins, functional RNAs (antisense, hammerhead ribozymes, RNAi), and the like. One well-known example is the cystic fibrosis transmembrane conductance regulator (CFTR) gene. The primary physiological defect in cystic fibrosis is the failure of electrogenic chloride ion secretion across the epithelia of many organs, including the lungs. One of the most dangerous aspects of the disorder is the cycle of recurrent airway infections, which gradually destroy lung function resulting in premature death. Cystic fibrosis is caused by a variety of mutations in the CFTR gene. Since the problems arising in cystic fibrosis result from mutations in a single gene, the possibility exists that the introduction of a normal copy of the gene into the lung epithelia could provide a treatment for the disease, or effect a cure if the gene transfer was permanent.

Other disorders resulting from mutations in a single gene (known as monogenic disorders), which can be treated by the compositions herein include alpha-1-antitrypsin deficiency, chronic granulomatous disease, familial hypercholesterolemia, Fanconi anemia, Gaucher disease, Hunter syndrome, ornithine transcarbamylase deficiency, purine nucleoside phosphorylase deficiency, severe combined immunodeficiency disease (SCID)-ADA, X-linked SCID, hemophilia, retinitis pigmentosa, muscular dystrophy, and the like.

Therapeutic benefit in other disorders may also result from the addition of a protein-encoding therapeutic nucleic acid. For example, addition of a nucleic acid encoding an immunomodulating protein such as interleukin-2 may be of therapeutic benefit for patients suffering from different types of cancer. In many cases, a gene encoding a protein or peptide can have therapeutic benefit, even if the underlying disorder is not genetically based. For example, the gene for vascular endothelial growth factor, VEGF, may be introduced to treat cardiac or peripheral ischemia. Conversely, DNA encoding soluable VEGF receptors or RNAi species that reduce or counteract VEGF mRNA may be valuable as antiangiogenesis agents for the treatment of cancer or macular degeneration A nucleic acid fragment of interest may additionally be a "marker nucleic acid" or "marker polypeptide". Marker genes encode proteins, which can be easily detected in transformed cells and are, therefore, useful in the study of those cells. Marker genes are being used in bone marrow transplantation studies, for example, to investigate the biology of marrow reconstitution and the mechanism of relapse in patients. Examples of suitable marker genes include beta-galactosidase, green or yellow fluorescent proteins, chloramphenicol acetyl transferase, luciferase, and the like.

A nucleic acid fragment of interest may additionally be a control region. The term "control region" or "control element" includes all nucleic acid components, which are operably linked to a nucleic acid fragment (e.g., DNA) and involved in the expression of a protein or RNA therefrom. The precise nature of the control (or regulatory) regions needed for coding sequence expression may vary from organism to organism. Such regions typically include those 5' noncoding sequences involved with initiation of transcription and translation, such as the enhancer, TATA box, capping sequence, CAAT sequence, and the like. Further exemplary control sequences include, but are not limited to, any sequence that functions to modulate replication, transcriptional or translational regulation, and the like. Examples include promoters, signal sequences, propeptide sequences, transcription terminators, polyadenylation sequences, enhancer sequences, attenuatory sequences, intron splice site sequences, and the like.

A nucleic acid fragment of interest may additionally be a trait-producing sequence, by which it is meant a sequence conferring some non-native trait upon the organism or cell in which the protein encoded by the trait-producing sequence is expressed. The term "non-native" when used in the context of a trait-producing sequence means that the trait produced is different than one would find in an unmodified organism which can mean that the organism produces high amounts of a natural substance in comparison to an unmodified organism, or produces a non-natural substance. For example, the genome of a crop plant, such as corn, can be modified to produce higher amounts of an essential amino acid, thus creating a plant of higher nutritional quality, or could be modified to produce proteins not normally produced in plants, such as antibodies. (See U.S. Pat. No. 5,202,422 (issued Apr. 13, 1993); U.S. Pat. No. 5,639,947 (Jun. 17, 1997).) Likewise, the genomes of industrially important microorganisms can be modified to make them more useful such as by inserting new metabolic pathways with the aim of producing novel metabolites or improving both new and existing processes such as the production of antibiotics and industrial enzymes. Other useful traits include herbicide resistance, antibiotic resistance, disease resistance, resistance to adverse environmental conditions (e.g., temperature, pH, salt, drought), and the like.

Methods of transforming cells are well known in the art. By "transformed" it is meant a heritable alteration in a cell resulting from the uptake of foreign DNA. Suitable methods include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, RNAi, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence, which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., and normalized by Gribskov, Nucl. Acids Res. 14(6):6745-USA, 6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, homology can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.)

A first polynucleotide is "derived from" a second polynucleotide if it has the same or substantially the same basepair sequence as a region of the second polynucleotide, its cDNA, complements thereof, or if it displays sequence identity as described above.

A first polypeptide is "derived from" a second polypeptide if it is (i) encoded by a first polynucleotide derived from a second polynucleotide, or (ii) displays sequence identity to the second polypeptides as described above.

In the present invention, when a recombinase is "derived from a phage" the recombinase need not be explicitly produced by the phage itself, the phage is simply considered to be the original source of the recombinase and coding sequences thereof. Recombinases can, for example, be produced recombinantly or synthetically, by methods known in the art, or alternatively, recombinases may be purified from phage infected bacterial cultures.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

2. Overview

Site-specific recombination is characterized by a strand exchange mechanism that requires no DNA synthesis or high-energy cofactor; the phosphodiester bond energy is conserved in a phospho-protein linkage during strand cleavage and re-ligation (Stark, Boocock and Sherratt 1992).

Two unrelated families of site-specific recombinases are currently known. The first, called the 'phage integrase' or, more informatively, the tyrosine recombinase family, groups >100 enzymes that have a tyrosine-catalyzed reaction mechanism (Nunes-Duby et al. 1998). The second, called the 'resolvase' or serine recombinase family, groups >100 enzymes that have a serine-catalyzed reaction mechanism (Smith and Thorpe 2002). These enzymes have an N-terminal catalytic and dimerization domain that contains a conserved serine residue involved in the transient covalent attachment to DNA. The extended arm at the C-terminus of this domain connects to the C-terminal helix-turn-helix DNA-binding domain of the resolvases in this group.

Site-specific recombinases carry out recombination between two recognition sites that can be identical or different. For example, Cre resolvase, a member of the tyrosine site-specific recombinase family, carries out recombination between two identical 34-bp long loxP sites. Cre has been widely used, for example, in vivo to create deletions and other rearrangements in mice (Sauer 1994) and other species and in vitro in the Creator system for providing rapid cloning of fragments into various vector backbones. The related FLP resolvase has also been used extensively to perform rearrangements in vivo (O'Gorman, Fox and Wahl 1991). Lambda integrase, a phage integrase in the tyrosine recombinase family, carries out unidirectional recombination between a 25-bp long attB site and a 243-bp long attP site. Lambda integrase has found widespread use in vitro in the Gateway cloning system.

3. Serine Integrases

While the Cre, FLP, and lambda tyrosine site-specific recombinase systems have extensive utility, further novel and useful properties are associated with recombinases from the evolutionarily unrelated serine site-specific recombinase family, both in vivo and in cell-free reactions. Of special interest in this group is the subfamily of long unidirectional serine phage integrases typified by phage phiC31 integrase (Kuhstoss and Rao 1991; Thorpe and Smith 1998). These integrases carry out unidirectional recombination between unlike attB and attP recognition sites that are typically of minimal sizes between 30-50 bp (Groth and Calos 2004; Groth et al. 2000).

Some of the favorable properties of these serine integrases include the following: (1) their lack of co-factor requirements. This feature means that in vitro reactions proceed in simple buffers. In addition, the enzymes carry out robust reactions in many cellular environments in many species, in some cases including efficient interaction with inserted att sites or with endogenous pseudo att sites in mammalian and other eukaryotic chromosomes; (2) the availability of many characterized family members of these enzymes, each with different DNA recognition specificities. This feature means that the enzymes can be used separately or in combination to create the opportunity for more complex or sequential DNA manipulations; (3) lack of a topology requirement. Circular, supercoiled, relaxed circle, or linear molecules are efficient substrates for the enzymes, opening up possibilities not available with more restricted recombinases; and (5) unidirectional, with compact attB and attP sites. This feature means that reaction products are stable and not reversible. This property is especially critical for obtaining a high net integration efficiency. Through these features, the serine integrases offer unique advantages for performing DNA manipulations. No other group of recombinases possesses this combination of properties.

The serine integrases include phiC31, R4, TP901-1, A118, U153, phiFC1, Bxb1, phiBT1, phiRV-1, and others, many of which are enumerated by Smith and Thorpe (2002). Additional members of the serine integrase family are being discovered, through isolation and characterization of new bacteria and phages and through sequencing projects. In either case, polypeptides can be assigned to the serine integrase group by two properties. First, a homologous catalytic domain encompassing a catalytic serine residue, usually occupying the amino-terminal ~140 amino acids of the protein and recognizable by a distinct secondary and tertiary structure, is common to all serine recombinases. Secondary structure prediction programs make the strong prediction that all of these catalytic domains have a similar structure, consisting of alternating beta sheet and alpha helix segments occupying approximately 140 amino acids.

All enzymes of the serine recombinase family, not just those that are integrases, possess this characteristically folded catalytic domain. In some cases, this catalytic domain is not amino terminal in the non-integrase members, but it is still a recognizable structure. The three dimensional crystal structure of the gamma delta resolvase solved at 3.0 Angstrom resolution by Yang and Steitz (1995) appears to be representative of the structure of the catalytic domain of the whole group and matches the secondary structure prediction closely. Therefore, it can be assumed that the 3-D structure of the catalytic domain of other serine recombinase family members will be similar to that solved for gamma delta. A common reaction mechanism involving a concerted cut-and-paste reaction and strand exchange across a 2-base pair core sequence is also likely to be shared among the group.

A second distinguishing feature of the serine integrase family is a carboxy terminal portion of the protein that is unusually long for the serine recombinases, resulting in proteins that are 450 to over 600 amino acids long. We have demonstrated that these long serine integrases possess the features listed above, having small attB and attP sites, working without host co-factors, and functioning in heterologous cells including eukaryotic cells such as mammalian cells. Through our analysis of many members of this family, it has become clear that these features are general for the serine integrases and inherent to them (Groth and Calos 2004; Groth et al. 2000; Olivares, Hollis and Calos 2001; Stoll, Ginsberg and Calos 2002). Therefore, future family members yet to be discovered, classified to the group on the basis of amino acid sequence homology and structural similarity, are expected to exhibit these same properties and to share a similar reaction mechanism.

In addition to shared secondary and tertiary structural features in their catalytic domains, the serine integrases share the functional features of being unidirectional recombinases. That is, unlike resolvases that exchange two identical sites, integrases recombine two sites that are different in sequence, attB and attP. After reaction, two hybrid sites (attL and attR) are created that are not actionable by the integrase alone (Thorpe, Wilson and Smith 2000). An accessory excisionase protein is required to perform the reverse reaction. This feature gives inherent directionality to the reaction that is useful for stabilizing desired outcomes, such as integration events. The attB and attP sites are typically composed of partial palindromes arranged, often somewhat asymmetrically, around a 2-bp core. The serine integrases are highly suitable for both in vitro cloning reactions and in vivo vector or genome manipulations, with features more versatile and advantageous than those of any other type of site-specific recombinase over a broad range of applications.

The wild-type members of the serine integrase class of enzymes have already demonstrated utility in genome engineering in yeast (Thomason, Calendar and Ow 2001), *Drosophila* (Groth et al. 2004), plants (Luta et al. 2004), and mammals (Groth et al. 2000). See U.S. Pat. No. 6,632,672, which is incorporated herein by reference in its entirety for all purposes. Building upon this utility, we introduced the concept of altered recombinases that are optimized by the investigator for features desirable in a given application, such as a higher frequency of integration or a greater binding preference for a non-wild-type att site, termed a pseudo att site. See U.S. Pat. No. 6,808,925, which is incorporated herein by reference in its entirety for all purposes. Such altered recombinases could potentially be created by many means.

For example, random mutagenesis to create a pool of integrase mutants, followed by DNA shuffling and screening (Stemmer 1994) was used to create mutant integrases with a preference for an endogenous sequence on human chromosome 8 (Sclimenti, Thyagarajan and Calos 2001). This pseudo attP site has a partial sequence match (44% identity) to the phiC31 integrase wild-type attP site (Thyagarajan et al. 2001). The most successful mutants in this study had several amino acid changes spread over the length of the integrase protein. The best altered integrases, obtained after two cycles of DNA shuffling and screening, had a 2-3-fold increase in frequency of reaction at the targeted site on chromosome 8 in the human genome and a ~5-fold gain in specificity. These relatively modest gains in specificity and activity were obtained at the cost of an overall 10-fold lower integration frequency, compared to the wild-type phiC31 integrase. This approach to generating altered integrases may have limited utility in creating enzymes that have both high specificity and high efficiency.

A more extreme form of mutagenesis, which creates what is termed a "hybrid integrase" or a "hybrid recombinase", is disclosed here. This idea allows us to create enzymes with heightened utility. The hybrid integrase concept involves fusing an improved catalytic domain having integrase activity with a DNA binding domain (e.g., foreign or non-native DNA binding domain), providing site-specificity for the integration reaction. The foreign DNA binding domain may be from a related protein such as another serine integrase, or it may be derived from an unrelated naturally occurring protein such as a transcription factor or from a synthetic protein such as a designed DNA binding domain.

The hybrid integrase concept utilizes structural features of the serine recombinases that are distinct from those of the tyrosine recombinases. The serine recombinases possess discrete domains encompassing the catalytic and DNA binding portions of the protein. These two domains contact the DNA of the target site separately and are connected by a short linker region (Yang and Steitz 1995). As demonstrated for the Tn3 resolvase, a serine recombinase that is not an integrase, this modular feature allows a foreign DNA binding domain to be attached to the catalytic domain to create a functional resolvase in vitro and in *E. coli* that now exhibits an altered DNA recognition specificity (Akopian et al. 2003)

One way we utilize this modular feature is by creating fusions encompassing a deliberately optimized catalytic domain derived from one serine integrase, fused to the DNA binding domain derived from another recombinase family member, to confer different binding specificity on the hybrid recombinase. For example, we have demonstrated function of many serine integrases in mammalian cells. Each integrase has a distinct recognition sequence. However, most of these integrases have poor reaction efficiency with mammalian chromosomes, catalyzing integration at a frequency below that of random integration. Therefore, these native proteins have limited utility for genome modification. Their utility can be expanded by fusion of their DNA binding domain to a more active catalytic domain, such as those derived from integrases phiC31 or R4 that have a more robust reaction with mammalian chromosomal sequences.

In addition, the idea of creating an integrase with designed specificity can be achieved by fusing an optimized serine integrase catalytic domain with foreign DNA binding domains from other classes of proteins, such as zinc finger binding proteins. Zinc fingers of the Cys2His2 class are one of the most abundant DNA-binding motifs found in eukaryotes (Elrod-Erickson and Pabo 1999). These zinc finger proteins recognize a diverse set of DNA sequences. Design and selection efforts have produced many variant fingers with modified specificities. The first zinc finger-DNA complex to be visualized at atomic resolution involved the three fingers of Zif268 (Pavletich and Pabo 1991). The structure of the Zif268-DNA complex revealed that each finger contains a short, two-stranded antiparallel beta sheet and an alpha helix. The sheet and the helix are held together by a small hydrophobic core and by a zinc ion, which is coordinated by two conserved cysteines from the sheet region and two conserved histidines from the alpha helix. Each of the fingers uses residues from the amino-terminal portion of its alpha helix to contact bases in the major groove, each finger making its primary contacts with a three base pair subsite (GCG/TGG/GCG).

The manner of interaction of zinc finger domains with DNA sequences has been sufficiently described so that it is possible to design zinc finger domains that will bind to many 9-bp DNA sequences (Tan et al. 2003). The zinc finger technology represents a powerful approach to obtaining designed targeting of integration. To target integration by using zinc finger domains, the DNA binding domain is fused to a catalytic domain that can carry out DNA cutting and ligation at the location directed by the zinc finger domain. The modular enhanced catalytic domain of a serine phage integrase such as phiC31 is the most efficient such moiety described to date and therefore represents the best partner for the designed zinc finger domain in the goal of creating site-specific integrases with designed specificities.

While some serine phage integrases like phiC31 have an inherent ability to utilize mammalian chromosomal sequences as a substrate, this ability can be optimized by mutagenesis. Our studies of integration mediated by serine integrases into mammalian genomes indicate that chromosome context also plays an important role in ability to act upon a particular chromosomal sequence as a substrate. This information cannot be derived from studies in bacteria.

In one strategy, we utilize structural information inherent to the organization of the serine catalytic domain and its active site to make directed mutations that alter the reaction kinetics and efficiency of the enzymes in different conditions. These changes are informed by comparison of the amino acid sequences of other serine recombinase family members and by introducing substitutions that are functionally tolerated by some family members into other members at cognate positions. We also introduce mutations found to be favorable in family members to increase activity in other settings. Candidate mutants are assayed in the desired setting, such as human cells. Some favorable mutations can be combined to create an additive or synergistic effect. The result is a catalytic domain optimized for integration in a particular setting such as mammalian chromosomes. Another strategy focuses on screening the activity of integrases derived genes mutated at random or by directed processes such as substitution of charged residues with alanine.

The combination of an artificially optimized catalytic domain with a foreign DNA binding domain creates a novel class of integrases that can perform desired reactions at higher efficiencies and with different DNA sequence specificities than the parent recombinase enzymes.

We have shown that some modulation is possible regarding which pre-existing genomic hotspot sites are used by phiC31 integrase, by performing directed evolution (Sclimenti, Thyagarajan and Calos 2001). However, only limited gains in specificity of a few fold were possible with this approach after two rounds of DNA shuffling and screening, and additional rounds did not provide further improvement. While preference for one target site was modestly improved, the overall efficiency of integration was depressed 10-fold, diminishing the advantages of greater specificity (Sclimenti, Thyagarajan and Calos 2001). As a result, to date altered integrases produced by these methods have not found utility.

In addition, both the wild-type and the shuffled integrases characterized to date still recognize degenerate sites in the genome at many locations. The relatively low level of specificity for endogenous sites or pre-placed att sites in mammalian genomes leads to the potential for integration at undesired locations and for reaction between chromosomal sites, which could produce translocations or other unwanted chromosome rearrangements.

It may not be possible to perform optimization of specificity and optimization of integration frequency simultaneously on the same molecule. Rather, if optimization of integration frequency is carried out on the catalytic domain, and this domain is fused to a DNA binding domain optimized for the desired DNA binding characteristics, a more effective way to construct the integrase of interest may result. Thus, it may be better to construct an integrase in a modular way, ending with a hybrid integrase, rather than to optimize multiple features of the enzyme as a single polypeptide chain.

An important advantage of a hybrid integrase with a tight-binding DNA recognition domain is that a greater degree of sequence specificity is possible. For example, a zinc finger DNA binding domain binds more strongly to DNA than a native phage integrase does. This higher affinity of binding mediates greater specificity so that unique sequences can be targeted, free of adventitious side reactions that could produce undesired integration events or chromosome aberrations. For example, it has been shown that a zinc finger transcription factor can target a particular 18-bp recognition sequence, targeting just a single gene in the human genome (Tan et al. 2003). This level of specificity is higher than that seen to date with wild-type or altered phage integrases (Sclimenti, Thyagarajan and Calos 2001; Thyagarajan et al. 2001). Therefore, site-specific recombination tools with a higher level of safety and precision can be created with the hybrid integrase approach than with any approach previously described. The ability to create efficient integrases of predetermined sequence specificity truly opens up new vistas for genetic engineering.

These types of precisely directed changes at present can only be performed by homologous recombination, which is a low efficiency process that becomes even more inefficient with larger size of the inserted DNA and smaller size of flanking homology. Homologous recombination frequency has been improved through the use of targeted positioning of double-strand breaks. However, even if a technology were perfected to insert such double-strand breaks precisely and efficiently, the homologous recombination process still generally occurs at a frequency of 1% or less. There are probably natural limitations on its efficiency, because it is an endogenous genetic process that is tied into multiple regulatory mechanisms and also affects endogenous chromosomal recombination. The frequency of homologous recombination is too low to provide effective gene therapy. Directed changes can be performed with higher efficiency if an enzyme with integrase activity is fused to a DNA-binding domain with precise recognition specificity.

4. Applications

The hybrid recombinases herein have multiple utilities, including but not limited to, genomic research and therapeutics. For example the hybrid recombinases herein can be utilized in gene therapy.

Targeting Hybrid Recombinases

The present invention provides a means for targeted insertion of a polynucleotide (or nucleic acid sequence(s)) of interest into a genome by, for example, (i) providing a hybrid recombinase, wherein the hybrid recombinase is capable of facilitating recombination between a first recombination site (designed site or vector site) and a second recombination site (target site), (ii) providing a targeting construct having a first recombination sequence and a polynucleotide of interest, (iii) introducing the hybrid recombinase and the targeting construct into a cell which contains in its nucleic acid the second recombination site, wherein said introducing is done under conditions that allow the hybrid recombinase to facilitate a recombination event between the first and second recombination sites.

Historically, the attachment site in a bacterial genome is designated "attB" and in a corresponding bacteriophage the site is designated "attP". A recombination site in a cell of interest is designated herein as "attT" (target site). A recombination site in a targeting vector is referred to herein as "attD" (designed site).

In one aspect of the present invention, the hybrid serine integrase includes an improved catalytic domain fused to a foreign DNA binding domain. The foreign DNA binding domain may be from a related protein such as another serine integrase, or it may be from an unrelated naturally occurring protein such as a transcription factor or from a synthetic protein such as a designed DNA binding domain.

Introducing Hybrid Recombinase

In the methods of the invention a site-specific hybrid recombinase is introduced into a cell whose genome is to be modified. Methods of introducing functional proteins into cells are well known in the art. Introduction of purified recombinase protein ensures a transient presence of the protein and its function, which is often a preferred embodiment. Integrase can also be introduced into the target cell as its corresponding mRNA. The integrase mRNA can, for example, be microinjected into the target cells (Groth et al. 2004). Alternatively, a gene encoding the hybrid recombinase can be included in an expression vector used to transform the cell. It is generally preferred that the hybrid recombinase be present for only such time as is necessary for insertion of the nucleic acid fragments into the genome being modified. Thus, the lack of permanence associated with protein, mRNA, and most expression vectors is not expected to be detrimental.

The hybrid recombinases used in the practice of the present invention can be introduced into a target cell before, concurrently with, or after the introduction of a targeting vector. The hybrid recombinase can be directly introduced into a cell as a protein, for example, using liposomes, coated particles, or microinjection. Alternately, a polynucleotide encoding the hybrid recombinase can be introduced into the cell using a suitable expression vector. The targeting vector components described above are useful in the construction of expression cassettes containing sequences encoding a hybrid recombinase of interest. Expression of the hybrid recombinase is typically desired to be transient. Accordingly, vectors providing transient expression of the hybrid recombinase are preferred in the practice of the present invention. However, expression of the hybrid recombinase can be regulated in other ways, for example, by placing the expression of the hybrid recombinase under the control of a regulatable promoter (i.e., a promoter whose expression can be selectively induced or repressed).

Sequences encoding recombinases useful in the practice of the present invention are known and include, but are not limited to, the following: Cre—Sternberg, et al., J. Mol. Biol. 187:197-212; phiC31—Kuhstoss and Rao, J. Mol. Biol. 222:897-908, 1991; TP901-1-Christiansen, et al., J. Bact. 178:5164-5173, 1996; R4—Matsuura, et al., J. Bact. 178:3374-3376, 1996, PhiBT1—Gregory et al. 2003.

Hybrid recombinases for use in the practice of the present invention can be produced recombinantly or purified as previously described. Polypeptides having the desired recombinase activity can be purified to a desired degree of purity by methods known in the art of protein purification, including, but not limited to, size fractionation, ammonium sulfate precipitation, affinity chromatography, HPLC, ion exchange chromatography, heparin agarose affinity chromatography (e.g., Thorpe & Smith, Proc. Nat. Acad. Sci. 95:5505-5510, 1998.)

Gene Therapy

Gene therapy applications usually require long-term gene expression. Such expression can often most easily be obtained by integration of the therapeutic gene into the genome. We have demonstrated the utility of the phage integrase phiC31 to provide such long-term gene expression for gene therapy applications in mouse liver (Olivares et al. 2002) and in human skin (Ortiz-Urda et al. 2003; Ortiz-Urda et al. 2002). We have also demonstrated that the integrase works well in muscle, eye, blood cells, and others.

The wild-type phiC31 integrase targets a number of sequences in the human genome that bear partial identity to the phage attP site. Hotspot sites also probably have favorable context features that enable the integrase access these sites more easily. However, the integration sites utilized by phiC31 and other site-specific phage integrases are directed by the integrase's inherent DNA binding preference and are not chosen by the investigator. Therefore, the chromosomal location of the sites is not under experimental control. Some of the integration sites may be undesirable from the point of view of safety and efficacy.

With the wild-type phage integrase technology, one is not able to target the integration event to an endogenous location desired by the investigator. If targeting were possible, one could, for example, choose an area of the genome for maximal safety, such as an area where other genes would not be disrupted or influenced by the inserted gene. Alternatively, one could position the inserted genetic material so that it will bring about a desired change in the genome, such as activation of a desired gene product, such as erythropoietin, or disruption of an undesired gene product, such as a dominant negative gene product. Another option is introduction of a correct portion of a gene at a relevant position, such as within an intron, such that the correct portion of the gene will be spliced in place of a mutant form to remove a common mutation, as in the cystic fibrosis transmembrane receptor.

Thus, in one embodiment, the invention comprises a method of treating a disorder in a subject in need of such treatment, wherein at least one cell or cell type (or tissue, etc.) of the subject has a target recombination sequence (designated attT). This cell(s) is transformed with a nucleic acid construct (a "targeting construct") comprising a second recombination sequence (designated attD) and one or more polynucleotides of interest (typically a therapeutic gene). Into the same cell a hybrid recombinase is introduced that specifically recognizes the recombination sequences under conditions such that the nucleic acid sequence of interest is inserted into the genome via a recombination event between attT and attD. Subjects treatable using the methods of the invention include both humans and non-human organisms (e.g., animals, plants). Such methods utilize the targeting constructs and hybrid recombinases of the present invention.

A variety of disorders may be treated by employing the method of the invention including monogenic disorders, infectious diseases, acquired disorders, cancer, and the like. Exemplary monogenic disorders include severe combined immunodeficiency disease (SCID)-ADA, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, thalassaemias, retinitis pigmentosa, Xeroderma pigmentosa, ataxia telangiectasia, Bloom's syndrome, retinoblastoma, Tay-Sach's disease, alpha-1-antitrypsin deficiency, familial hypercholesterolemia, ornithine transcarbamylase deficiency, purine nucleoside phosphorylase deficiency, hemophilia, and the like.

Infectious diseases treatable by employing the methods of the invention include infection with various types of virus including human T-cell lymphotropic virus, influenza virus, papilloma virus, hepatitis virus, herpes virus, Epstein-Bar virus, immunodeficiency viruses (HIV, and the like), cytomegalovirus, and the like. Also included are infections with other pathogenic organisms such as *Mycobacterium tuberculosis, Mycoplasma pneumoniae*, and the like or parasites such as *Plasmodium falciparum*, and the like.

The term "acquired disorder" as used herein refers to a noncongenital disorder. Such disorders are generally considered more complex than monogenic disorders and may result from inappropriate or unwanted activity of one or more genes. Examples of such disorders include peripheral artery disease, rheumatoid arthritis, coronary artery disease, cancer, diabetes, Parkinson's disease, macular degeneration, diabetic retinopathy, and the like.

A particular group of acquired disorders treatable by employing the methods of the invention include various cancers, including both solid tumors and hematopoietic cancers such as leukemias and lymphomas. Solid tumors that are treatable utilizing the invention method include carcinomas, sarcomas, osteomas, fibrosarcomas, chondrosarcomas, and the like. Specific cancers include breast cancer, brain cancer, lung cancer (non-small cell and small cell), colon cancer, pancreatic cancer, prostate cancer, gastric cancer, bladder cancer, kidney cancer, head and neck cancer, and the like.

The suitability of the particular place in the genome for integration is dependent in part on the particular disorder being treated. For example, if the disorder is a monogenic disorder and the desired treatment is the addition of a therapeutic nucleic acid encoding a non-mutated form of the nucleic acid thought to be the causative agent of the disorder, a suitable place may be a region of the genome that does not encode any known protein and which allows for a reasonable expression level of the added nucleic acid.

The nucleic acid construct useful in this embodiment is additionally comprised of one or more nucleic acid fragments of interest. Preferred nucleic acid fragments of interest for use in this embodiment are therapeutic genes and/or control regions, as previously defined. The choice of nucleic acid sequence will depend on the nature of the disorder to be treated. For example, a nucleic acid construct intended to treat hemophilia B, which is caused by a deficiency of coagulation factor IX, may comprise a nucleic acid fragment encoding functional factor IX. A nucleic acid construct intended to treat obstructive peripheral artery disease may comprise nucleic acid fragments encoding proteins that stimulate the growth of new blood vessels, such as, for example, vascular endothelial growth factor, platelet-derived growth factor, and the like. Those of skill in the art would readily recognize which nucleic acid fragments of interest would be useful in the treatment of a particular disorder.

The nucleic acid construct can be administered to the subject being treated using a variety of methods. Administration can take place in vivo or ex vivo. By "in vivo," it is meant in the living body of an animal. By "ex vivo" it is meant that cells or organs are modified outside of the body. Such cells or organs are typically returned to a living body.

Methods for the therapeutic administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995, all of which are incorporated by reference herein), using viral vectors (Monahan, et al, Gene Therapy 4:40-49, 1997; Onodera, et al, Blood 91:30-36, 1998, all of which are incorporated by reference herein), by uptake of "naked DNA", electroporation, pulsed electrode avalanche device, and the like. Techniques well known in the art for the transfection of cells (see discussion above) can be used for the ex vivo administration of nucleic acid constructs. The exact formulation, route of administration and dosage can be chosen by the individual physician in view of the patient's condition. (See e.g. Fingl et al., 1975, in "The Pharmacological Basis of Therapeutics", Ch. 1 pl).

It should be noted that the attending physician would know how to and when to terminate, interrupt, or adjust administration due to toxicity, to organ dysfunction, and the like. Conversely, the attending physician would also know how to adjust treatment to higher levels if the clinical response were not adequate (precluding toxicity). The magnitude of an administered dose in the management of the disorder being treated will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

In general at least 1-10% of the cells targeted for genomic modification should be modified in the treatment of a disorder. Thus, the method and route of administration will optimally be chosen to modify at least 0.1-1% of the target cells per administration. In this way, the number of administrations can be held to a minimum in order to increase the efficiency and convenience of the treatment.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

The subject being treated will additionally be administered a hybrid recombinase that specifically recognizes the attT and attD recombination sequences that are selected for use. The particular recombinase can be administered by including a nucleic acid encoding it as part of a nucleic acid construct, or as a protein to be taken up by the cells whose genome is to be modified. Methods and routes of administration will be similar to those described above for administration of a targeting construct comprising a recombination sequence and nucleic acid sequence of interest. The hybrid recombinase protein is likely to only be required for a limited period of time for integration of the nucleic acid sequence of interest. Therefore, if introduced as a hybrid recombinase gene, the vector carrying the hybrid recombinase gene will lack sequences mediating prolonged retention. For example, conventional plasmid DNA decays rapidly in most mammalian cells. The hybrid recombinase gene may also be equipped with gene expression sequences that limit its expression. For example, an inducible promoter can be used, so that hybrid recombinase expression can be temporally limited by limited exposure to the inducing agent. One such exemplary group of promoters are tetracycline-responsive promoters the expression of which can be regulated using tetracycline or doxycycline.

Stem Cells.

It has become apparent that both embryonic and adult stem and progenitor cells have the capacity to stimulate the repair of tissue damage in tissues such as heart, brain, blood, spinal cord, and potentially liver, pancreas, and many others. Often, the capacity of a stem cell to perform repair can be enhanced if a gene is added. For example, the capacity to repair damage resulting from heart attacks appears to be enhanced by the secretion of growth factors such as VEG-F from stem cells positioned in regions of damage.

Currently, conventional retroviruses, lentivirus vectors, and other random integration methods are the primary tools used to modify stem cells. As in gene therapy, random integration has the capacity to initiate tumors and it also often results in poor expression of the inserted genes. Therefore, precise site-specific placement of inserted genes in stem cells would increase the safety and efficacy of stem cell therapeutic approaches.

Transgenic Organisms.

In another embodiment, the present invention comprises transgenic plants and nonhuman transgenic animals whose genomes have been modified by employing the methods and compositions herein. Transgenic animals may be produced employing the methods of the present invention to serve as a model system for the study of various disorders and for screening of drugs that modulate such disorders.

A "transgenic" plant or animal refers to a genetically engineered plant or animal, or offspring of genetically engineered plants or animals. A transgenic plant or animal usually contains material from at least one unrelated organism, such as, from a virus. The term "animal" as used in the context of transgenic organisms means all animal species except human. It also includes an individual animal in all stages of development, including embryonic and fetal stages. Farm animals (e.g., chickens, pigs, goats, sheep, cows, horses, rabbits and the like), rodents (such as mice), and domestic pets (e.g., cats and dogs) are included within the scope of the present invention. In a preferred embodiment, the animal is a mouse or a rat.

The term "chimeric" plant or animal is used to refer to plants or animals in which the heterologous gene is found, or in which the heterologous gene is expressed in some but not all cells of the plant or animal.

The term transgenic animal also includes a germ cell line transgenic animal. A "germ cell line transgenic animal" is a transgenic animal in which the genetic information provided by the invention method has been taken up and incorporated into a germ line cell, therefore conferring the ability to transfer the information to offspring. If such offspring, in fact, possess some or all of that information, then they, too, are transgenic animals.

Methods of generating transgenic plants and animals are known in the art and can be used in combination with the teachings of the present application.

In one embodiment, a transgenic animal of the present invention is produced by introducing into a single cell embryo a nucleic acid construct, comprising an attD recombination site capable of recombining with an attT recombination site found within the genome of the organism from which the cell was derived and a nucleic acid fragment of interest, in a manner such that the nucleic acid fragment of interest is stably integrated into the DNA of germ line cells of the mature animal and is inherited in normal Mendelian fashion.

In this embodiment, the nucleic acid fragment of interest can be any one of the fragments described previously. Alternatively, the nucleic acid sequence of interest can encode an exogenous product that disrupts or interferes with expression of an endogenously produced protein of interest, yielding a transgenic animal with decreased expression of the protein of interest.

A variety of methods are available for the production of transgenic animals. A nucleic acid construct of the invention can be injected into the pronucleus, or cytoplasm, of a fertilized egg before fusion of the male and female pronuclei, or injected into the nucleus of an embryonic cell (e.g., the nucleus of a two-cell embryo) following the initiation of cell division (Brinster, et al., Proc. Nat. Acad. Sci. USA 82: 4438, 1985). Embryos can be infected with viruses, especially retroviruses, modified with an attD recombination site and a nucleic acid sequence of interest. The cell can further be treated with a site-specific recombinase as described above to promote integration of the nucleic acid sequence of interest into the genome.

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099-1112, 1990). Rodents suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47:897-905, 1991). Other procedures for introduction of DNA into tissues of animals are described in U.S. Pat. No. 4,945,050 (Sandford et al., Jul. 30, 1990).

Totipotent or pluripotent stem cells derived from the inner cell mass of the embryo and stabilized in culture can be manipulated in culture to incorporate nucleic acid sequences employing invention methods. A transgenic animal can be produced from such cells through injection into a blastocyst that is then implanted into a foster mother and allowed to come to term.

Methods for the culturing of stem cells and the subsequent production of transgenic animals by the introduction of DNA into stem cells using methods such as electroporation, calcium phosphate/DNA precipitation, microinjection, liposome fusion, retroviral infection, and the like are also are well known to those of ordinary skill in the art. See, for example, Teratocarcinomas and Embryonic Stem Cells, A Practical Approach, E. J. Robertson, ed., IRL Press, 1987). Reviews of standard laboratory procedures for microinjection of heterologous DNAs into mammalian (mouse, pig, rabbit, sheep, goat, cow) fertilized ova include: Hogan et al., Manipulating the Mouse Embryo (Cold Spring Harbor Press 1986); Krimpenfort et al., 1991, Bio/Technology 9:86; Palmiter et al., 1985, Cell 41:343; Kraemer et al., Genetic Manipulation of the Early Mammalian Embryo (Cold Spring Harbor Laboratory Press 1985); Hammer et al., 1985, Nature, 315:680; Purcel et al., 1986, Science, 244:1281; Wagner et al., U.S. Pat. No. 5,175,385; Krimpenfort et al., U.S. Pat. No. 5,175,384, the respective contents of which are incorporated by reference.

The final phase of the procedure is to inject targeted ES cells into blastocysts and to transfer the blastocysts into pseudopregnant females. The resulting chimeric animals are bred and the offspring are analyzed by Southern blotting or PCR to identify individuals that carry the transgene. Procedures for the production of non-rodent mammals and other animals have been discussed by others (see Houdebine and Chourrout, supra; Pursel, et al., Science 244:1281-1288, 1989; and Simms, et al., Bio/Technology 6:179-183, 1988).

The term transgenic as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with loss of function that has been achieved by use of the invention vector. In one embodiment, transgenic animals having gene knockouts are those in which the target gene has been rendered nonfunctional by an insertion targeted to the gene to be rendered non-functional by targeting a pseudo-recombination site located within the gene sequence.

Examples of many gene therapy, stem cell, transgenic animal and plant, gene expression, cell line, and protein production applications are described in U.S. Pat. No. 6,632,672, U.S. Pat. No. 6,808,925, and international patent application no. PCT/US03/17702, which applications are incorporated herein by reference in their entirety.

Cells and Protein Production

Cell lines are often used as model systems to study biological phenomena. Great advantage can be taken in this setting of manipulating the cell line by addition of defined sequences, to gain information about effects of particular genes, control sequences, and the like. Because of the prevalence of context effects on gene expression in higher cells, it is desirable to control the chromosomal context of inserted genes. The development of efficient site-directed integration would enable these kinds of studies to be carried out in a precise and reproducible way, and the quality of the data obtained would be superior to results obtained with random integration.

The ability to reproducibly position incoming genes at desired locations would also greatly enhance the efficiency of protein production methods in cultured cells and in organisms.

Cells suitable for modification employing the methods of the invention include both prokaryotic cells and eukaryotic cells. Prokaryotic cells are cells that lack a defined nucleus. Examples of suitable prokaryotic cells include bacterial cells, mycoplasmal cells and archaebacterial cells. Particularly preferred prokaryotic cells include those that are useful either in various types of test systems (discussed in greater detail below) or those that have some industrial utility such as *Klebsiella oxytoca* (ethanol production), *Clostridium acetobutylicum* (butanol production), and the like (see Green and Bennet, Biotech & Bioengineering 58:215-221, 1998; Ingram, et al, Biotech & Bioengineering 58:204-206, 1998). Suitable eukaryotic cells include both animal cells (such as from insect, rodent, cow, goat, rabbit, sheep, non-human primate, human, and the like) and plant cells (such as rice, corn, cotton, tobacco, tomato, potato, and the like). Cell types applicable to particular purposes are discussed in greater detail below.

Yet another embodiment of the invention comprises isolated genetically engineered cells. Suitable cells may be prokaryotic or eukaryotic, as discussed above. The genetically engineered cells of the invention may be unicellular organisms or may be derived from multicellular organisms. By "isolated" in reference to genetically engineered cells derived from multicellular organisms it is meant the cells are outside a living body, whether plant or animal, and in an artificial environment. The use of the term isolated does not imply that the genetically engineered cells are the only cells present.

In one embodiment, the genetically engineered cells of the invention contain any one of the nucleic acid constructs of the invention. In a second embodiment, a hybrid recombinase that specifically recognizes recombination sequences is introduced into genetically engineered cells containing one of the nucleic acid constructs of the invention under conditions such that the nucleic acid sequence(s) of interest will be inserted into the genome. Thus, the genetically engineered cells possess a modified genome. Methods of introducing such hybrid recombinases are well known in the art and are discussed above.

The genetically engineered cells of the invention can be employed in a variety of ways. Unicellular organisms can be modified to produce commercially valuable substances such as recombinant proteins, industrial solvents, industrially useful enzymes, and the like. Preferred unicellular organisms include fungi such as yeast (for example, *S. pombe, Pichia pastoris, S. cerevisiae* (such as INVSc1), and the like) *Aspergillis*, and the like, and bacteria such as *Klebsiella, Streptomyces*, and the like.

Isolated cells from multicellular organisms can be similarly useful, including insect cells, mammalian cells, and plant cells. Mammalian cells that may be useful include those derived from rodents, primates and the like. They include HeLa cells, cells of fibroblast origin such as VERO, 3T3 or CHOK1, HEK 293 cells or cells of lymphoid origin (such as 32D cells) and their derivatives. Preferred mammalian host cells include nonadherent cells such as CHO, 32D, and the like.

In addition, plant cells are also available as hosts, and control sequences compatible with plant cells are available, such as the cauliflower mosaic virus 35S and 19S, nopaline synthase promoter and polyadenylation signal sequences, and the like. Appropriate transgenic plant cells can be used to produce transgenic plants.

Another preferred host is an insect cell, for example from the *Drosophila* larvae. Using insect cells as hosts, the *Drosophila* alcohol dehydrogenase promoter can be used (Rubin, Science 240:1453-1459, 1988). Alternatively, baculovirus vectors can be engineered to express large amounts of peptide encoded by a desired nucleic acid sequence in insect cells (Jasny, Science 238:1653, 1987); Miller et al., In: Genetic Engineering (1986), Setlow, J. K., et al., eds., Plenum, Vol. 8, pp. 277-297).

The genetically engineered cells of the invention are additionally useful as tools to screen for substances capable of modulating the activity of a protein encoded by a nucleic acid fragment of interest. Thus, an additional embodiment of the invention comprises methods of screening comprising contacting genetically engineered cells of the invention with a test substance and monitoring the cells for a change in cell phenotype, cell proliferation, cell differentiation, enzymatic activity of the protein or the interaction between the protein and a natural binding partner of the protein when compared to test cells not contacted with the test substance.

A variety of test substances can be evaluated using the genetically engineered cells of the invention including peptides, proteins, antibodies, low molecular weight organic compounds, natural products derived from, for example, fungal or plant cells, and the like. By "low molecular weight organic compound" it is, meant a chemical species with a molecular weight of generally less than 500-1000. Sources of test substances are well known to those of skill in the art.

Various assay methods employing cells are also well known by those skilled in the art. They include, for example, assays for enzymatic activity (Hirth, et al, U.S. Pat. No. 5,763, 198, issued Jun. 9, 1998), assays for binding of a test substance to a protein expressed by the genetically engineered cells, assays for transcriptional activation of a reporter gene, and the like.

Cells modified by the methods of the present invention can be maintained under conditions that, for example, (i) keep them alive but do not promote growth, (ii) promote growth of the cells, and/or (iii) cause the cells to differentiate or dedifferentiate. Cell culture conditions are typically permissive for the action of the hybrid recombinase in the cells, although regulation of the activity of the hybrid recombinase may also be modulated by culture conditions (e.g., raising or lowering the temperature at which the cells are cultured). For a given cell, cell-type, tissue, or organism, culture conditions are known in the art.

Another category of genome manipulations that is useful, both in cell-free cloning reactions and in living cells, is to use recombinases to precisely engineer exchanges from one DNA molecule to another. There are several categories of such reactions, all of which can be addressed with hybrid recombinases.

Another useful reaction involves using hybrid serine integrases to create intramolecular deletions. For example on can create mini-vectors with hybrid recombinases. For example, for gene therapy the site-specific recombination activity of hybrid recombinases can be used to excise efficiently all undesired accessory sequences on a vector (often termed "backbone"), effectively creating a mini-plasmid containing only the therapeutic gene of interest. One can also create intrachromosomal deletions or inversions with hybrid recombinases.

5. Kits

The present invention also contemplates kits including one or more vials or containers. In one embodiment, one or more vials in a kit include hybrid recombinase(s) disclosed herein. In one embodiment, additional vial(s) can include target constructs. The kit can also include instructions on how to use the hybrid recombinase(s) and target construct(s) included therein.

EXAMPLES

Example 1

Creation of a Hybrid Serine Integrase by Introducing the DNA Binding Domain from Another Serine Integrase The phiC31 integrase has proven useful for integrating into mammalian genomes at a limited number of endogenous sites and at an efficiency of approximately 5% of transfected cells. The integrase may be even more useful if integration efficiency were increased. In addition, some pseudo attP sites recognized by the enzyme may be undesirable for gene therapy. For example, the psA pseudo site used in some cell types lies in an intron of the DLC-1 gene, which may be a tumor suppressor. Integration at this position, if it inactivates the DLC-1 gene, could increase cancer risk in cells bearing the integration.

To improve the integrase, we create an enhanced catalytic domain that possesses mutations that increase the ability of the enzyme to carry out the integration reaction in mammalian chromosomes. These mutations are generated by a mutagenesis process and/or by directed changes informed by comparison with other serine recombinases, followed by screening for higher activity.

A different set of pseudo att sites is provided by fusing the enhanced phiC31 integrase catalytic domain to the DNA binding domain of another serine integrase, phiBT1. The DNA sequence encoding the enhanced phiC31 catalytic domain is fused to the carboxy terminal portion of the phiBT1 integrase, at a point in the linker region of the phiBT1 integrase after the catalytic domain, in the vicinity of amino acid positions 140-150.

The hybrid integrase is tested for function at phiBT1 att sites on plasmids introduced into *E. coli* and mammalian cells. The hybrid enzyme can mediate reaction at phiBT1 att sites, but no longer mediates reaction at phiC31 att sites.

The chromosomal integration efficiency in human cells is tested by introducing the hybrid integrase, along with an assayable plasmid carrying the phiBT1 attP site, into human cells. Integrants are isolated and the integrated plasmid is recovered by plasmid rescue. The pseudo attB site used by the hybrid integrase is characteristic of the phiBT1 integrase, not the phiC31 integrase.

When a wild-type phiBT1 attB site is introduced into the genome, it is recognized by the hybrid integrase, but not by the phiC31 integrase. Conversely, the hybrid integrase does not mediate integration targeted to a phiC31 attP site that has been inserted into the genome. These results indicated that the hybrid integrase has enhanced integration efficiency and a new integration specificity that is contributed by the phiBT1 DNA binding domain.

Example 2

Creation of a Hybrid Serine Integrase that Combines an Improved Catalytic Domain with a Zinc Finger DNA Recognition Domain The phiC31 integrase has proven useful for integrating into mammalian genomes at a limited number of endogenous sites and at an efficiency of approximately 5% of transfected cells. The integrase may be even more useful if integration efficiency were increased. In addition, integration may be desired at sequences that are not native pseudo attP sites. For example, in gene therapy it may be desirable to insert transcriptional control signals at various locations in the genome.

To develop an integrase that can fulfill these requirements, we create an enhanced catalytic domain that possesses amino acid changes that increase the ability of the enzyme to carry out the integration reaction in mammalian chromosomes. These changes are generated by a mutagenesis process and/or by directed changes informed by structural and other information, followed by screening for higher activity.

The DNA sequence encoding the enhanced phiC31 catalytic domain is fused to a zinc finger DNA-binding domain. The hybrid integrase is tested for function at artificial att sites containing binding sites for the zinc finger protein on plasmids introduced into *E. coli* and mammalian cells. The hybrid enzyme can mediate reaction at zinc finger att sites, but no longer mediates reaction at phiC31 att sites.

The chromosomal integration efficiency in human cells is tested by introducing the hybrid integrase, along with an assayable plasmid carrying the zinc finger att site, into human cells. Integrants are isolated and the integrated plasmid is recovered by plasmid rescue. The chromosomal zinc finger binding site used by the hybrid integrase is characteristic of the zinc finger protein, not the phiC31 integrase.

When a wild-type zinc finger binding site is introduced into the genome by an integrase into a favorable hotspot position, it is recognized by the hybrid integrase, but not by the phiC31 integrase. Conversely, the hybrid integrase does not mediate integration targeted to a phiC31 attP site that has been inserted into the genome. These results indicate that the hybrid integrase has enhanced integration efficiency and a new integration specificity that is contributed by the zinc finger DNA binding domain.

Example 3

A functional phiBT1-phiC31 Hybrid

The literature suggests that the serine site-specific recombinases are constructed in a dual domain fashion, with an amino-(N) terminal catalytic domain of 120-150 amino acids and a carboxy-(C) terminal domain of variable length that encompasses the remainder of the protein, presumably including the DNA binding domain (Smith and Thorpe 2002). Because there is some resemblance between the N-terminal ~120-150 amino acids of the serine recombinases, especially at the secondary structure level, we hypothesized that these catalytic domains could be swapped between related family members, conferring novel DNA recognition specificities based on the properties of the C-terminal DNA-binding domain.

To investigate this issue, we first chose to join the C-terminal DNA-binding domain of the phiC31 integrase (Kuhstoss and Rao 1991) with the catalytic domain of the related phiBT1 integrase (Gregory, et al. 2003). A prediction of the hypothesis above would be that this hybrid enzyme would demonstrate integrase function at phiC31 attachment sites, because of the presence of the phiC31 DNA binding domain.

It was not possible to predict with complete accuracy exactly where to join the two domains of the related proteins to retain integrase function. To illuminate this issue, before constructing the intended hybrid, an analysis of primary and secondary structure relationship between the phiC31 and phiBT1 integrases was performed. These studies indicated that the N-terminal regions of the two integrases had similar secondary structures. The N-terminal region of the two integrases also showed greater similarity in primary amino acid sequence, compared to the C-terminal region. Based upon these results, it was decided that two candidate fusion, or joining, points would be tested. As shown in FIG. 1, the two fusion points were termed "120" and "168" for their approximate position in the phiBT1 sequence. There is some ambiguity in the naming scheme, because the crossover points were made in regions of identity/strong homology.

Figure 2:
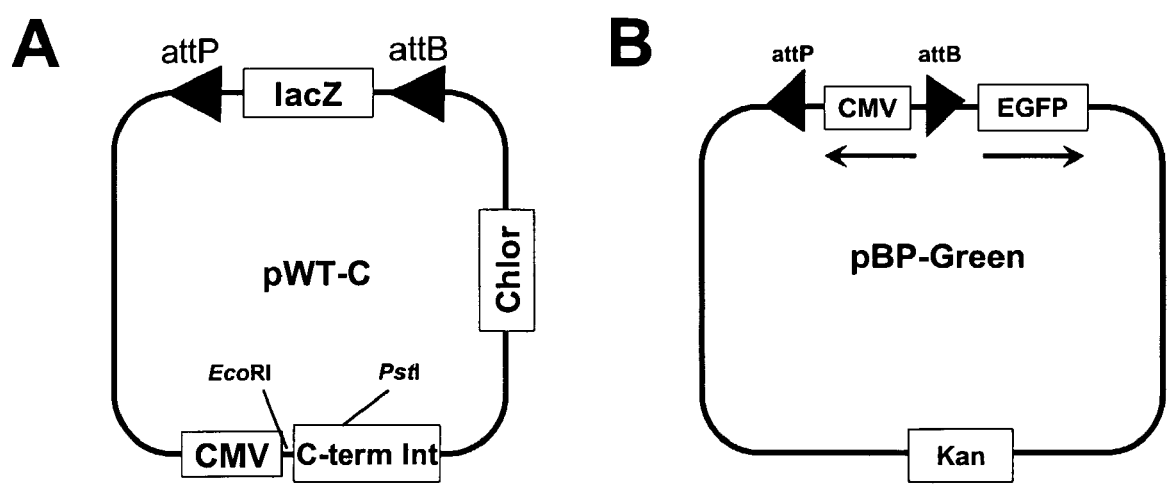
FIG. 2 illustrates plasmids used to create and assay hybrid integrases.

To construct these hybrids, the desired N-terminal sequence was synthesized with EcoRI/PstI ends using described methods, and cloned into the EcoRI/PstI sites of vector pWT-C (FIG. 2A), to generate hybrids 120 and 168. The vector pWT-C carried the C-terminal region of the phiC31 integrase gene from amino acids 167 to 613, driven by an uncharacterized bacterial promoter and the mammalian CMV promoter. To facilitate cloning, the plasmid pWT-C was designed with a PstI site that would allow in frame fusions of N-terminal sequences with the phiC31 C-terminal sequence (FIG. 2A). This PstI site spanned amino acids 167 and 168 in the wild-type phiC31 integrase.

In addition, this vector had a bacterial lacZ expression cassette flanked by phiC31 attB and attP sites. Upon recombination between the two att sites, the lacZ gene was excised. If no recombination took place, the lacZ expression cassette was retained. When cloning of a relevant piece of DNA results in a functional integrase protein, the lacZ expression cassette was excised and the resulting colony was white on a LB-agar plate containing X-gal. If the result of the cloning was a non-functional integrase, the lacZ expression cassette was retained, and the resulting colony was blue. Therefore, cloning integrase derivatives into the vector pWT-C allowed the immediate evaluation of integrase function.

Because the catalytic domain of these hybrids was contributed by phiBT1, which is less active than phiC31, the activity of hybrid clones was expected to be reduced when compared to wild-type phiC31. The reduced activity might not be sufficient to excise lacZ from all assay plasmids, leaving some blue color in the colonies. Thus both white and blue colonies were screened for integrase activity. Hybrid 120 was isolated as a blue colony. Restriction analysis of the plasmid DNA gave no indication of a recombinant fragment in the vicinity of the att sites, indicating little or no integrase activity. Hybrid 168 was isolated as a light blue colony. Restriction analysis of the plasmid DNA revealed that a large fraction of the plasmid DNA was recombined site-specifically at the phiC31 attB and attP sites, indicating abundant integrase activity.

To confirm these results, the 120 and 168 hybrid integrases were individually transfected into 293 cells along with extra-chromosomal assay plasmid pBCPB (Groth, et al. 2000), and the recombination reaction was allowed to take place for 72 hours. This assay plasmid carried the lacZ gene flanked by phiC31 attB and attP sites. Recombination between the att sites resulted in deletion of lacZ, producing a white colony in E. coli. DNA was recovered from 293 cells and electroporated into E. coli for evaluation. In this assay, hybrid 168 was half as efficient as the wild-type phiC31 integrase in recombining the attB and attP sites. The wild-type phiC31 control yielded ~65% white colonies, while the 168 hybrid yielded ~36%. In contrast, hybrid 120 yielded only 4.9% white colonies, which was not significantly different from the negative control. Therefore, again hybrid 120 showed no significant recombination activity, whereas hybrid 168 showed substantial integrase activity.

A portion of the DNA was also subjected to attL PCR, specific for the novel attL junction, to detect small amounts of recombined plasmid DNA. The attL sequence was a hybrid of attB and attP formed upon recombination and was diagnostic of phiC31-mediated site-specific recombination. The attL region was detected by PCR in samples treated with hybrid 168, but not hybrid 120. These results indicated that hybrid 120 was indeed not functional on phiC31 att sites (no PCR band and no significant number of white colonies), while hybrid 168 functioned significantly.

Figure 3:
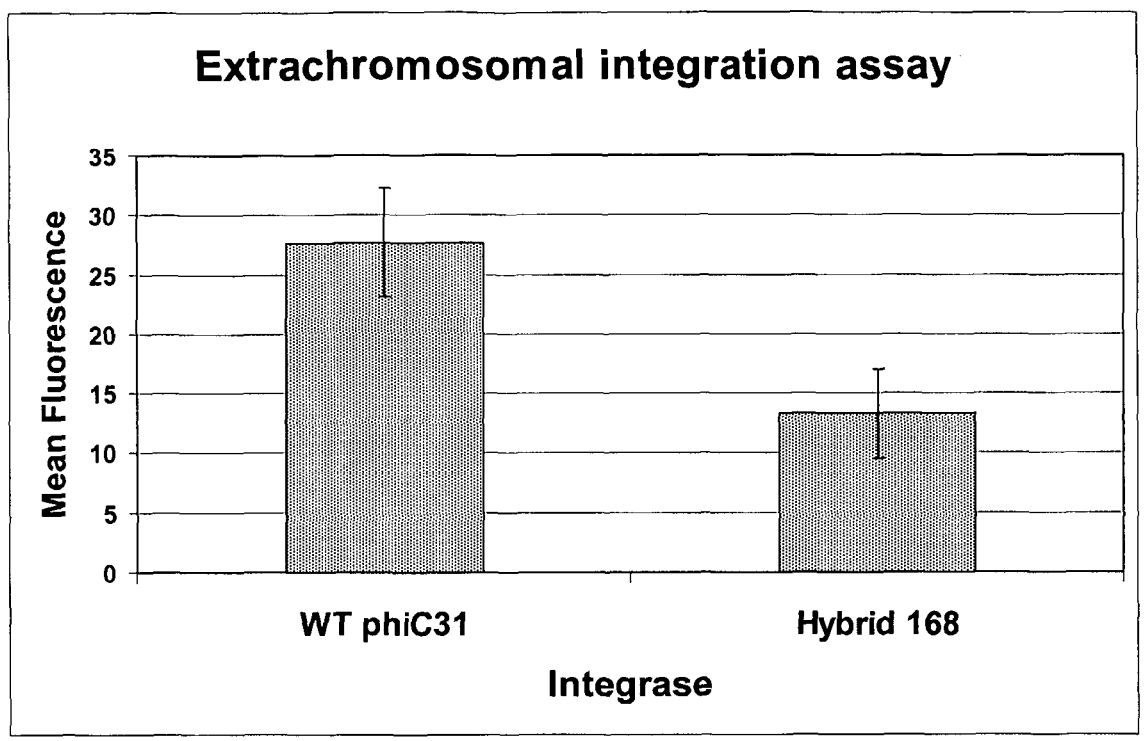
FIG. 3 illustrates hybrid 168 functional in a mammalian extrachromosomal assay. Plasmids expressing either phiC31 integrase or hybrid 168 were transfected into 293 cells along with substrate plasmid pBP-Green. Site-specific recombination resulted in expression of GFP. Mean fluorescence of the transfected cells was measured 72 hours after transfection using the Guava PCA-96 analyzer. Error bars represent the standard deviation.

The ability of hybrid 168 to perform recombination at wild-type phiC31 att sites in mammalian cells was further confirmed in two additional ways, an extrachromosomal inversion assay and a chromosomal integration assay. In the extrachromosomal assay, plasmid 168-1 expressing hybrid 168 was transfected into human 293 cells along with the extrachromosomal assay "flipper" plasmid pBP-Green (FIG. 2B), containing a promoterless GFP marker gene adjacent to an inverted CMV promoter that was flanked by wild-type phiC31 attB and attP sites. The att sites were oriented so that recombination between them led to inversion of the CMV promoter and expression of GFP by connecting it to the CMV promoter in the correct orientation for transcription. The mean GFP fluorescence was therefore a measure of the amount of recombination catalyzed by the integrase. Level of GFP fluorescence was assayed with a Guava analyzer after 72 hours. The results of this assay confirmed that hybrid 168 could catalyze recombination between phiC31 att sites (FIG. 3). Hybrid 168 was approximately half as efficient as wild-type phiC31 integrase in catalyzing this reaction, in keeping with the lesser activity of the phiBT1 integrase, the source of the catalytic domain in hybrid 168.

Figure 4:
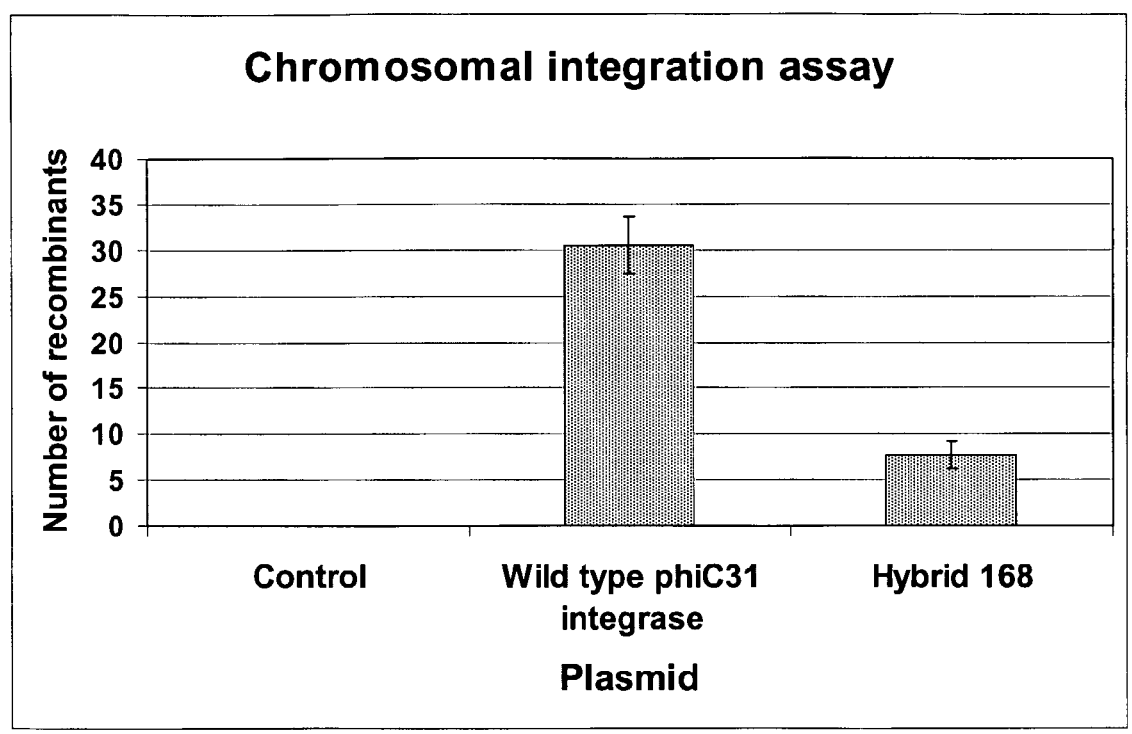
FIG. 4 illustrates hybrid 168 is functional in a mammalian chromosomal assay. Plasmids expressing phiC31 integrase, hybrid 168, or a control plasmid were transfected along with pNC-attB into 293-P3 cell line containing a phiC31 attP site in the chromosome. Site-specific recombination results in expression of a zeocin resistance marker. Selection was carried out on transfected cells for 14 days with zeocin (200 µg/ml) and the number of independent colonies was counted. Error bars represent the standard deviation.

In addition, the ability of hybrid 168 to integrate into a chromosomally placed phiC31 attP site was measured. Human cell line 293P3, containing plasmid pHZ-attP (Thyagarajan et al., 2001) carrying a wild-type phiC31 attP integrated into the chromosome (Thyagarajan, et al. 2001), was transfected with the hybrid 168 integrase plasmid (p168-1) or the plasmid pWT-FL, containing the full-length wild-type phiC31 expression cassette in the same backbone, along with donor plasmid pNC-attB (Thyagarajan et al., 2001) containing a phiC31 attB site and neomycin resistance gene. The cell line was designed such that site-specific integration of the donor into the chromosomal attP site would result in expression of a zeocin resistance gene that would render the cells resistant to zeocin antibiotic. As shown in FIG. 4, hybrid 168 catalyzed integration into a chromosomally placed phiC31 attP site. Wild-type phiC31 integrase was approximately 4-fold more efficient than hybrid 168, in keeping with the greater activity of phiC31 integrase in chromosomal integration, relative to phiBT1.

The integrase function and DNA recognition specificity of the phiBT1/C31 hybrid 168 demonstrated that it was possible to create active hybrid site-specific integrases that possessed the catalytic domain of one integrase and the DNA binding characteristics of another.

Example 4

A Functional GFP-phiC31 Integrase Hybrid

Increased site-specificity gained through fusion of integrase activity to highly specific DNA binding domains mights greatly enhance the utility of the phiC31 integrase. In addition, fusion of integrase to translocating peptides might facilitate its entry into target cells. In order to accomplish such objectives, integrase activity would need to remain functional when foreign protein domains were added to it. In order to determine if the phiC31 integrase could tolerate fusions with other proteins, we created a green fluorescent protein-phiC31 integrase hybrid and tested its ability to carry out recombination between phiC31 attB and attP.

Figure 5:
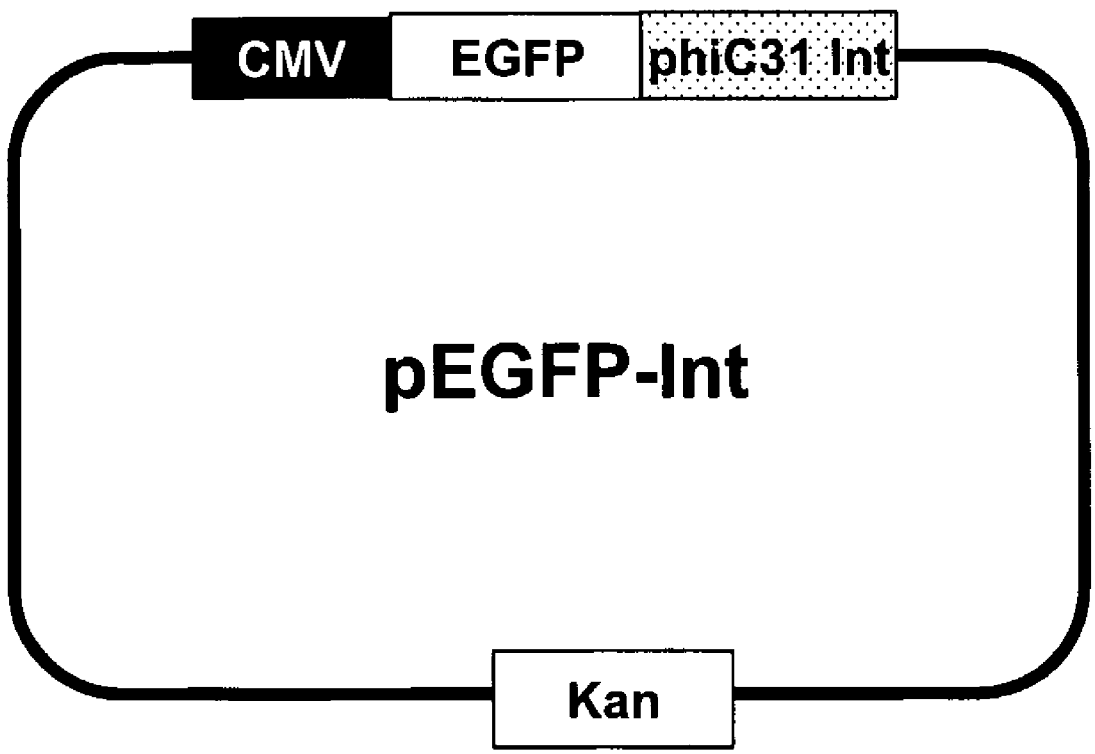
FIG. 5 illustrates a EGFP-Int fusion plasmid. pEGFP-Int has the full-length phiC31 integrase gene cloned in-frame with the EGFP gene in the plasmid pEGFP-C1 (BD Biosciences). The expression of the fusion protein is driven by the CMV promoter in mammalian cells.

Several commercially available vectors allow for cloning of a gene of interest in-frame with a marker gene to generate a fusion protein. For our purposes, we used the plasmid pEGFP-C1 (BD Biosciences), into which we cloned the full-length phiC31 integrase gene. The integrase gene was cloned into the plasmid such that the eGFP part of the fusion protein would form the N-terminal portion of the fusion protein, and the phiC31 integrase would form the C-terminal portion. The resulting plasmid construct, pEGFP-Int, is shown in FIG. 5.

We determined that this fusion protein was fluorescent in human 293 cells, as judged by analysis 24 hours after transfection with a Guava PCA-96 analyzer. The next step was to determine if the eGFP-Int fusion retained integrase function in mammalian cells. We used an extrachromosomal assay that used lacZ as a reporter for recombination. LacZ was flanked by phiC31 attB and attP sites, so upon recombination it was deleted. Assay plasmid pBCPB (Groth et al., 2000) was transfected into 293 cells, along with pEGFP-Int or pCMV-Int (Groth et al., 2000). The transfected cells were harvested 24 hours after transfection, and plasmid DNA was isolated from the cells. This DNA was transfected into *E. coli* cells, which were spread on plates containing X-gal and kanamycin. A functional integrase would generate a white colony, whereas a non-functional integrase would generate a blue colony. We found that the fusion protein was functional in 293 cells, generating 6.2% white colonies in the same experiment, while wild-type phiC31 integrase generated 9.7% white colonies. The negative control plasmid did not generate any white colonies. These results indicated that the fusion protein retained integrase activity.

Figure 6:
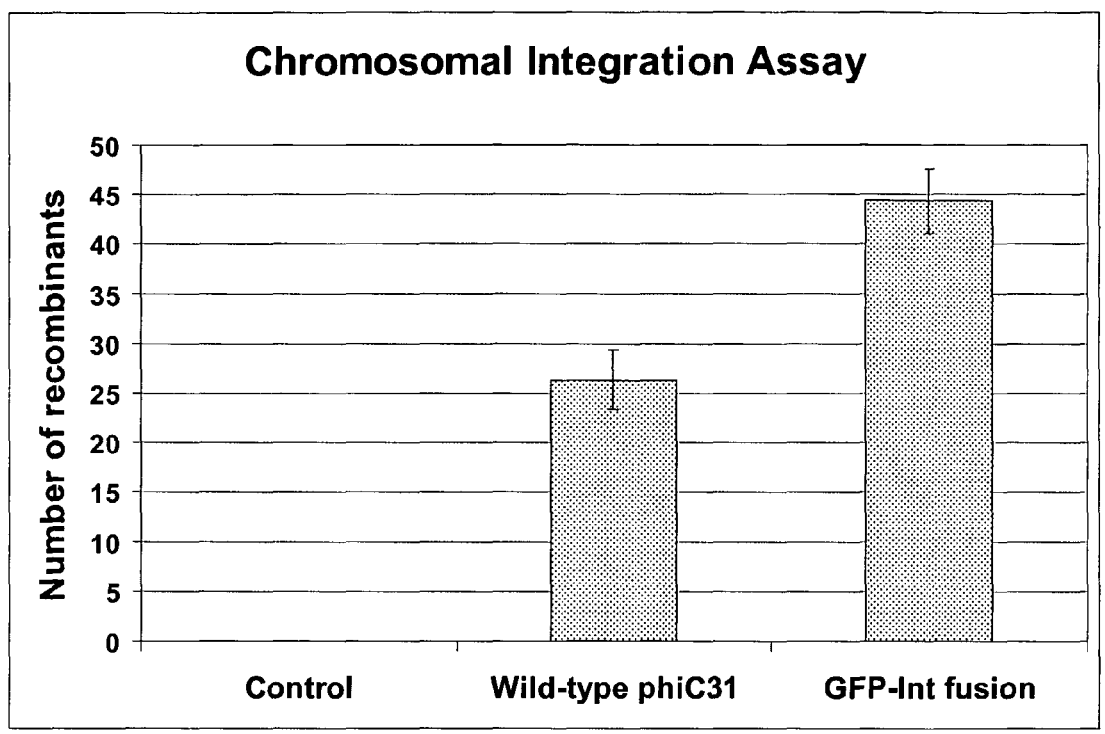
FIG. 6 illustrates GFP-Int fusion mediates chromosomal integration in mammalian cells. Plasmids expressing either phiC31 integrase, GFP-Int fusion, or a control were transfected into 293-P3 cell line along with donor plasmid pNC-attB. Site-specific recombination results in expression of a zeocin resistance marker. Selection was carried out on transfected cells for 14 days with zeocin (200 µg/ml), and the number of independent colonies was counted. Error bars represent the standard deviation.

Next, the ability of the fusion protein to perform chromosomal integration was studied. The plasmid pEGFP-Int was transfected into the 293P3 cell line, along with the donor plasmid pNC-attB (Thyagarajan et al., 2001). The cell line 293P3 contained an attP site placed in the chromosome, and the donor plasmid contained an attB site. Recombination between these two sites resulted in expression of a zeocin resistance gene. Selection for zeocin resistance allowed us to determine if a site-specific integration reaction occurred or not by counting the number of zeocin resistant colonies. As shown in FIG. 6, we found that the eGFP-Int fusion protein could perform recombination at a chromosomal attP site. The ability of the fusion protein to perform this reaction was not significantly different from that of the wild-type phiC31 integrase ($p > 0.1$).

We therefore proved the principle that the phiC31 integrase protein can tolerate fusions with foreign protein domains that can add to its functionality.

Example 5

A phiC31—Zinc Finger Hybrid Integrase

In order to create a functional integrase with DNA recognition specificity determined by a zinc finger protein, we fuse the catalytic domain of an altered phiC31 integrase with the Zif268 transcription factor (Pavletich and Pabo, 1991).

A fusion point is found by trying breakpoints in phiC31 integrase that include the catalytic domain. A fusion at amino acid 168 was successful in fusions between phiBT1 and phiC31 integrases, and may also be useful in creating the phiC31-Zif268 fusion. Fusions having breakpoints in that vicinity are created.

The hybrid enzymes are tested for function on synthetic "att" recognition sites that contain cores from the phiC31 integrase attB and attP sites that serve as the cross-over point, plus flanking 9-bp sequences encompassing the Zif268 recognition site (Pavletich and Pabo, 1991). A series of such artificial att sites with variable spacing between the core and recognition sites are synthesized and tested, to find the configuration that works best for recombination (Akopian et al. 2003). The best att sites are then used in the following assays.

The phiC31-Zif268 fusions are first tested in an extrachromosomal assay in human tissue culture cells. The assay plasmid contains synthetic attB and attP sites in inverted orientation, flanking a CMV promoter. Recombination between the sites inverts the promoter and places it adjacent to a flanking promoterless GFP gene, such that transcription of GFP is activated. Presence in the cells of green fluorescent protein is then assayed by reading the appropriate fluorescence signal on a Guava analyzer or FACS machine. The greater the GFP signal, the more recombination has occurred. In this way, the most active fusion can be identified.

Recombination mediated by the fusion is then tested in the context of a mammalian chromosome. The artificial attP site is placed in the chromosome and the artificial attB site is placed on a plasmid to be integrated. Ideally, the artificial attP site is placed into the chromosome by a site-specific integrase, so that a good chromosomal context surrounds the attP site. Recombination gives rise to a measurable signal, for example by providing a promoter to a promoterless antibiotic resistance gene (Thyagarajan et al, 2001) or activating transcription of a reporter gene such as GFP.

Recombination can be verified in the above assays by performing PCR that is specific for a junction fragment that would be created by the correct site-specific recombination event.

Once a phiC31-Zif268 fusion with site-specific recombinase activity has been demonstrated and the parameters for fusion location and att site structures are understood, it becomes possible to design custom integrase-Zif fusions for many desired target locations in the genome. For example, an appropriate genomic sequence that meets the criteria for an integrase cross-over core site is located. Zif proteins that recognize 9-bp sequences that are the appropriate distances on each side from the core are created, following the rules that have been developed for Zif recognition of DNA sequences (Tan et al. 2003).

Hybrid recombinases are created by fusing the amino terminal catalytic domain of the integrase with the Zif proteins, at locations that were successful in the Zif268 fusion. Integration mediated by the hybrid recombinases can be monitored in extrachromosomal and chromosomal assays as outlined above, following stable GFP expression or antibiotic resistance of plasmids bearing these marker genes and a synthetic attB site. The final endpoint would be demonstration of site-specific integration at the desired position in native genomic DNA. Success in this experiment represents creation of an integration system that recognizes a pre-specified target sequence that is native to the genome. Achievement of this goal opens up many opportunities for precise manipulation of the genome, including applications in gene therapy.

REFERENCES

Akopian, A., J. He, M. R. Boocock and W. M. Stark, 2003 Chimeric recombinases with designed DNA sequence recognition. Proc Natl Acad Sci USA 100: 8688-8691.

Elrod-Erickson, M., and C. Pabo, 1999 Binding studies with mutants of Zif268.

Gregory, M. A., Till, R., and Smith, M. C. M. (2003). Integration site for *Streptomyces* phage fBT1 and development of site-specific integrating vectors. J. Bacteriol. 185, 5320-5323.

Groth, A. C., and M. P. Calos, 2004 Phage integrases: biology and applications. J. Mol. Biol. 335: 667-678.

Groth, A. C., M. Fish, R. Nusse and M. P. Calos, 2004 Creation of transgenic *Drosophila* by using the site-specific integrase from phage phiC31. Genetics 166, 1775-1782.

Groth, A. C., E. C. Olivares, B. Thyagarajan and M. P. Calos, 2000 A phage integrase directs efficient site-specific integration in human cells. Proc. Natl. Acad. Sci. USA 97: 5995-6000.

Kuhstoss, S., and R. N. Rao, 1991 Analysis of the integration function of the Streptomycete bacteriophage FC31. J. Mol. Biol. 222: 897-908.

Luta, K. A., S. Corneille, A. K. Azhagiri, Z. Svab and P. Maliga, 2004 A novel approach to plastid transformation utilizes the phiC31 phage integrase. The Plant Journal 37: 906-913.

Nunes-Duby, S. E., H. J. Kwon, R. S. Tirumalai, T. Ellenberger and A. Landy, 1998 Similarities and differences among 105 members of the Int family of site-specific recombinases. Nucleic Acids Research 26: 391-406.

O'Gorman, S., D. T. Fox and G. M. Wahl, 1991 Recombinase-mediated gene activation and site-specific integration in mammalian cells. Science 251: 1351-1355.

Olivares, E. C., R. P. Hollis and M. P. Calos, 2001 Phage R4 integrase mediates efficient integration in mammalian cells. Gene 278: 167-176.

Olivares, E. C., R. P. Hollis, T. W. Chalberg, L. Meuse, M. A. Kay and M. P. Calos, 2002 Site-specific genomic integration produces therapeutic factor IX levels in mice. Nature Biotechnology 20: 1124-1128.

Ortiz-Urda, S., D. Keene, Q. Lin, M. P. Calos and P. Khavari, 2003 fC31 integrase-mediated nonviral genetic correction of junctional epidermolysis bullosa. Human Gene Therapy 14: 923-928.

Ortiz-Urda, S., B. Thyagarajan, D. Keene, Q. Lin, M. Fang, M. P. Calos and P. A. Khavari, 2002 Stable nonviral genetic correction of inherited human skin disease. Nature Medicine 8: 1166-1170.

Pavletich, N. P., and C. O. Pabo, 1991 Science 252: 809-817.

Sauer, B., 1994 Site-specific recombination: developments and applications. Current Opinion in Biotechnology 5: 521-527.

Sclimenti, C. R., B. Thyagarajan and M. P. Calos, 2001 Directed evolution of a recombinase for improved genomic integration at a native human sequence. Nucleic Acids Research 29: 5044-5051.

Smith, M. C. M., and H. M. Thorpe, 2002 Diversity in the serine recombinases. Molec. Microbiol. 44: 299-307.

Stark, W. M., M. R. Boocock and D. J. Sherratt, 1992 Catalysis by site-specific recombinases. Trends in Genetics 8: 432-439.

Stemmer, W. P. C., 1994 DNA shuffling by random fragmentation and reassembly: In vitro recombination for molecular evolution. Proc. Natl. Acad. Sci. USA 91: 10747-10751.

Stoll, S. M., D. S. Ginsberg and M. P. Calos, 2002 Phage TP901-1 site-specific integrase functions in human cells. J. Bacteriol. 184: 3657-3663.

Tan, S., D. Guschin, A. Davalos, Y. L. Lee, A. W. Snowden, Y. Jouvenot, H. S. Zhang, K. Howes, C. C. Case, C. O. Pabo, J. Campisi and P. D. Gregory, 2003 Zinc-finger protein-targeted gene regulation: Genomewide single-gene specificity. Proc Natl Acad Sci USA 100: 11997-12002.

Thomason, L. C., R. Calendar and D. W. Ow, 2001 Gene insertion and replacement in *Schizosaccharomyces pombe* mediated by the *Streptomyces* bacteriophage fC31 site-specific recombination system. Mol. Genet. Genomics 265: 1031-1038.

Thorpe, H. M., and M. C. M. Smith, 1998 In vitro site-specific integration of bacteriophage DNA catalyzed by a recombinase of the resolvase/invertase family. Proc. Natl. Acad. Sci. USA 95: 5505-5510.

Thorpe, H. M., S. E. Wilson and M. C. M. Smith, 2000 Control of directionality in the site-specific recombination system of the *Streptomyces* phage fC31. Mol. Microbiol. 38: 232-241.

Thyagarajan, B., E. C. Olivares, R. P. Hollis, D. S. Ginsburg and M. P. Calos, 2001 Site-specific genomic integration in mammalian cells mediated by phage fC31 integrase. Molecular and Cellular Biology 21: 3926-3934.

Yang, W., and T. A. Steitz, 1995 Crystal-structure of the site-specific recombinase gamma-delta resolvase complexed with a 34 bp cleavage site. Cell 82: 193-207.

What is claimed:

1. A hybrid recombinase comprising:
   a catalytic domain having a catalytic activity of a first recombinase derived from a phiC31 or phiBT1 bacteriophage organism; and
   a DNA binding domain having a DNA binding activity of a second recombinase derived from a phiC31 or phiBT1 bacteriophage organism, wherein said first recombinase and said second recombinase are different, and wherein said hybrid recombinase has said catalytic activity of said first recombinase, and said DNA binding activity of said second recombinase.

2. A pharmaceutical formulation comprising the hybrid recombinase of claim 1 and an excipient.

3. A kit comprising a first vial and instruction for use thereof, wherein said first vial comprises a hybrid recombinase of claim 1.

4. The hybrid recombinase of claim 1 further comprising a linker disposed between said catalytic domain and said DNA binding domain.

5. A nucleic acid encoding the hybrid recombinase of claim 1.

6. A vector for site-specific integration of a polynucleotide sequence into the genome of a eucaryotic cell, said vector comprising, (i) a circular backbone vector,
(ii) a nucleic acid of interest operably linked to a eucaryotic promoter, and
(iii) a single recombination site, wherein said single recombination site comprises a nucleic acid sequence that recombines with a second recombination site in the genome of said eukaryotic cell and said recombination occurs in the presence of a hybrid recombinase of claim 1.

7. The hybrid recombinase of claim 1 wherein the catalytic domain is derived from a phiBT1 bacteriophage integrase.

8. The hybrid recombinase of claim 7 wherein the catalytic domain is derived from amino acids 1-168 of the phiBT1 bacteriophage integrase gene.

9. The hybrid recombinase of claim 1 wherein the DNA binding domain is derived from a phiC31 bacteriophage integrase.

10. The hybrid recombinase of claim 1 wherein the DNA binding domain is derived from amino acids 166-613 of the phiC31 bacteriophage integrase gene.

11. The hybrid recombinase of claim 4 wherein the catalytic domain is derived from a phiC31 bacteriophage integrase and the DNA binding domain is derived from a phiBT1 bacteriophage integrase.

12. The hybrid recombinase of claim 11 wherein the phiC31 bacteriophage integrase catalytic domain and the phiBT1 bacteriophage integrase DNA binding domain are fused at a point between amino acid positions 140-150 of the linker region of the phiBT bacteriophage integrase.

* * * * *